US00PP21442P2

(12) United States Plant Patent

Valenzuela et al.

(10) Patent No.: US PP21,442 P2

(45) Date of Patent: Nov. 2, 2010

(54) *LIMONIUM* PLANT NAMED 'JSADA'

(50) Latin Name: *Limonium sinense*
Varietal Denomination: Jsada

(75) Inventors: Camilo Herrera Valenzuela, Bogotá (CO); Camilo Alejandro Chivatá Romero, Bogotá (CO)

(73) Assignee: C.I. Valmar S.A., Bogotá (CO)

( * ) Notice: Subject to any disclaimer, the term of this patent is extended or adjusted under 35 U.S.C. 154(b) by 0 days.

(21) Appl. No.: 12/383,841

(22) Filed: Mar. 27, 2009

(51) Int. Cl.
*A01H 5/00* (2006.01)

(52) U.S. Cl. ..... Plt./358

(58) Field of Classification Search ..... Plt./358, Plt./449

See application file for complete search history.

*Primary Examiner*—June Hwu
(74) *Attorney, Agent, or Firm*—C. A. Whealy

(57) ABSTRACT

A new and distinct cultivar of *Limonium* plant named 'Jsada', characterized by its erect, long and strong flowering stems; relatively large leaves; freely flowering habit; small white-colored flowers arranged in narrow inflorescences; and excellent postproduction longevity.

1 Drawing Sheet

Botanical designation: *Limonium sinense.*
Cultivar Denomination: 'Jsada'.

BACKGROUND OF THE INVENTION

The present invention relates to a new and distinct cultivar of *Limonium* plant, botanically known as *Limonium sinense*, commercially used as a cut flower *Limonium*, and hereinafter referred to by the name 'Jsada'.

The new *Limonium* plant is a product of a planned breeding program in Madrid, Cundinamarca, Colombia. The objective of the breeding program was to create new high-yielding *Limonium* cultivars that flower early and are resistant to pathogens.

The new *Limonium* plant originated from an open-pollination in Madrid, Cundinamarca, Colombia in February, 2006 of a proprietary selection of *Limonium sinense* identified as code number JS401003-3, not patented, as the female, or seed, parent with an unknown selection of *Limonium sinense* as the male, or seed, parent. The new *Limonium* plant was discovered and selected by the Inventors as a single flowering plant from within the progeny of the stated open-pollination grown in a controlled greenhouse environment in Madrid, Cundinamarca, Colombia on Oct. 24, 2006.

Asexual reproduction of the new *Limonium* plant by cuttings in a controlled greenhouse environment in Madrid, Cundinamarca, Colombia since February, 2007, has shown that the unique features of this new *Limonium* plant are stable and reproduced true to type in successive generations.

SUMMARY OF THE INVENTION

Plants of the new *Limonium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Jsada'. These characteristics in combination distinguish 'Jsada' as a new and distinct cultivar of *Limonium* plant:

1. Erect, long and strong flowering stems.
2. Relatively large leaves.
3. Freely flowering habit.
4. Small white-colored flowers arranged in narrow inflorescences.
5. Excellent postproduction longevity.

Plants of the new *Limonium* can be compared to plants of the female parent selection. Plants of the new *Limonium* differ from plants of the female parent selection in the following characteristics:

1. Plants of the new *Limonium* produced more flowering stems than plants of the female parent selection.
2. Plants of the new *Limonium* and the female parent selection differed in flower color as plants of the female parent selection had pink-colored flowers.

Plants of the new *Limonium* can be compared to plants of *Limonium sinense* 'Silver Diamond', not patented. In side-by-side comparisons conducted in Madrid, Cundinamarca, Colombia, plants of the new *Limonium* differed primarily from plants of 'Silver Diamond' in the following characteristics:

1. Plants of the new *Limonium* had straighter flowering stems than plants of 'Silver Diamond'.
2. Plants of the new *Limonium* had larger and flatter leaves than plants of 'Silver Diamond'.
3. Plants of the new *Limonium* had lighter green-colored flowering stems than plants of 'Silver Diamond'.
4. Inflorescences of plants of the new *Limonium* were not as open as inflorescences of plants of 'Silver Diamond'.
5. Flowers of plants of the new *Limonium* were positioned towards the apex of the flowering stems whereas flowers of plants of 'Silver Diamond' were positioned in the upper half of the flowering stems.

BRIEF DESCRIPTION OF THE PHOTOGRAPHS

The accompanying colored photographs illustrate the overall appearance of the new *Limonium* plant, showing the colors as true as it is reasonably possible to obtain in colored reproductions of this type. Colors in the photographs may differ slightly from the color values cited in the detailed botanical description which accurately describe the colors of the new *Limonium* plant.

The photograph in the center of the sheet comprises a side perspective view of a typical flowering stem of 'Jsada'.

The photograph on the upper left side of the sheet is a close-up view of a typical inflorescence of 'Jsada'.

The photograph on the upper right of the sheet is a close-up view of typical inflorescences of 'Jsada'.

The photograph on the bottom left of the sheet is a close-up view of the upper and lower surfaces of typical leaves of 'Jsada'.

The photograph on the bottom right of the sheet comprises a side perspective view of typical flowering plants of 'Jsada' grown in a ground bed.

DETAILED BOTANICAL DESCRIPTION

The aforementioned photographs and following observations and measurements describe plants of the new *Limonium* grown in ground beds in a polyethylene-covered greenhouse located in Madrid, Cundinamarca, Colombia. During the production of the plants, day temperatures ranged from 15° C. to 25° C., night temperatures ranged from 8° C. to 12° C. and light levels averaged 21.4 KWH/m$^2$ per week. Plants were pinched one time about six weeks after planting and were 18 weeks old when the description and photographs were taken. Color references are made to The Royal Horticultural Society Colour Chart, 2007 Edition, except where general terms of ordinary dictionary significance are used.

Botanical classification: *Limonium sinense* 'Jsada'.

Parentage:

*Female, or seed, parent.*—Proprietary selection of *Limonium sinense* identified as code number JS401003-3, not patented.

*Male, or pollen, parent.*—Unknown selection of *Limonium sinense*, not patented.

Propagation:

*Type.*—By cuttings.

*Time to initiate roots.*—About ten days with day temperatures ranging from 15° C. to 25° C. and night temperatures ranging from 8° C. to 12° C.

*Time to produce a rooted young plant.*—About four weeks with day temperatures ranging from 15° C. to 25° C. and night temperatures ranging from 8° C. to 12° C.

*Root description.*—Fleshy, medium in thickness; white in color.

*Rooting habit.*—Freely branching; dense.

Plant description:

*Appearance.*—Perennial subshrub grown as a cut flower; erect, long and strong flowering stems; inverted narrow triangle form; leaves basal and obovate in shape; freely flowering habit; numerous flowers arranged in symmetrical and open panicles; flowers positioned towards the apex of the flowering stem; vigorous growth habit.

*Branching habit.*—Freely basal branching habit, about 15 to 18 flowering stems develop per plant; pinching enhances branching potential.

*Plant height.*—About 97 cm.

*Plant diameter or spread.*—About 45 cm.

*Flowering stems.*—Length: About 87 cm. Spread, at the apex: About 25 cm. Diameter: About 5 mm. Internode length: About 6 cm. Strength: Strong. Texture: Smooth, glabrous; longitudinally ridged. Color: Close to 146A.

Foliage description:

*Arrangement.*—In a basal rosette, simple; sessile.

*Length.*—About 24 cm.

*Width.*—About 7.5 cm.

*Shape.*—Obovate.

*Apex.*—Obtuse.

*Base.*—Cuneate to attenuate.

*Margin.*—Entire.

*Texture, upper and lower surfaces.*—Smooth, glabrous.

*Venation pattern.*—Pinnate, reticulate.

*Color.*—Developing leaves, upper surface: Close to 146A. Developing leaves, lower surface: Close to 148B. Fully expanded leaves, upper surface: More green than 147A; venation, close to N137A. Fully expanded leaves, lower surface: More green than 147A; venation, close to 146A.

Flower description:

*Flower arrangement and habit.*—Open and symmetrical panicles with numerous flowers; flowers actinomorphic and symmetrical and arranged towards the apices of the inflorescences; freely flowering habit, about 650 flowers per flowering stem; flowers face mostly upright and outwardly; flowers sessile.

*Flowering response.*—In Colombia, plants flower year round; early flowering response, plants begin flowering about 17 weeks after planting.

*Post-production longevity.*—As a cut flower, flowers last for about 30 days; corolla not persistent, calyx persistent.

*Fragrance.*—Faint, pleasant.

*Inflorescence height.*—About 36 cm.

*Inflorescence diameter.*—About 8 cm to 12 cm.

*Flower diameter.*—About 5 mm to 6 mm.

*Flower depth (height).*—About 5 mm to 7 mm.

*Flower buds.*—Length: About 6 mm. Diameter: About 1.5 mm. Shape: Fusiform. Color: Close to NN155C to NN155D.

*Corolla.*—Petals per flower: About five in a single whorl, fused. Petal length: About 8 mm. Petal lobe width: About 2 mm. Petal shape: Narrowly deltoid to ligulate. Petal apex and margin lobe: Emarginate. Petal texture, upper and lower surfaces: Smooth, glabrous; satiny, membraneous. Petal color, upper and lower surfaces: Towards the base, close to 9A to 9B; midsection and towards the base, close to NN155C to NN155D.

*Calyx.*—Sepals per flower: About five in a single whorl, fused. Sepal length: About 8 mm. Sepal diameter: About 3 mm. Sepal shape: Deltoid. Sepal apex and lobe margin: Erose, fringed. Sepal texture, upper and lower surfaces: Smooth, glabrous; papery. Sepal color, upper and lower surfaces: Close to NN155C to NN155D; towards the base, close to 146C to 146D.

*Peduncles.*—Length: About 17 cm to 43 cm depending on position on the flowering stem. Diameter: About 1.5 mm to 2 mm. Strength: Strong, wiry, flexible. Angle: About 45° from stem axis. Texture: Smooth, glabrous; longitudinally ridged. Color: Close to 146A.

*Reproductive organs.*—Androecium: Stamen number: About five per flower. Filament length: About 2.5 mm. Filament color: Close to NN155C. Anther length: Less than 1 mm. Anther shape: Oblong. Anther color: Close to 6D. Amount of pollen: Scarce. Pollen color: Close to 6D. Gynoecium: Pistil number: One per flower. Pistil length: About 3 mm. Style length: About 2.5 mm. Style color: Close to NN155D. Stigma shape: Three-parted. Stigma color: Close to 6D. Ovary color: Close to 144A.

*Seeds/fruits.*—Seed and fruit development have not been observed.

Disease/pest resistance: Plants of the new *Limonium* have not been observed to be resistant to pathogens and pests common to *Limonium.*

Temperature tolerance: Plants of the new *Limonium* have been observed to tolerate temperatures from about −1° C. to about 30° C.

It is claimed:

1. A new and distinct *Limonium* plant named 'Jsada' as illustrated and described.

* * * * *

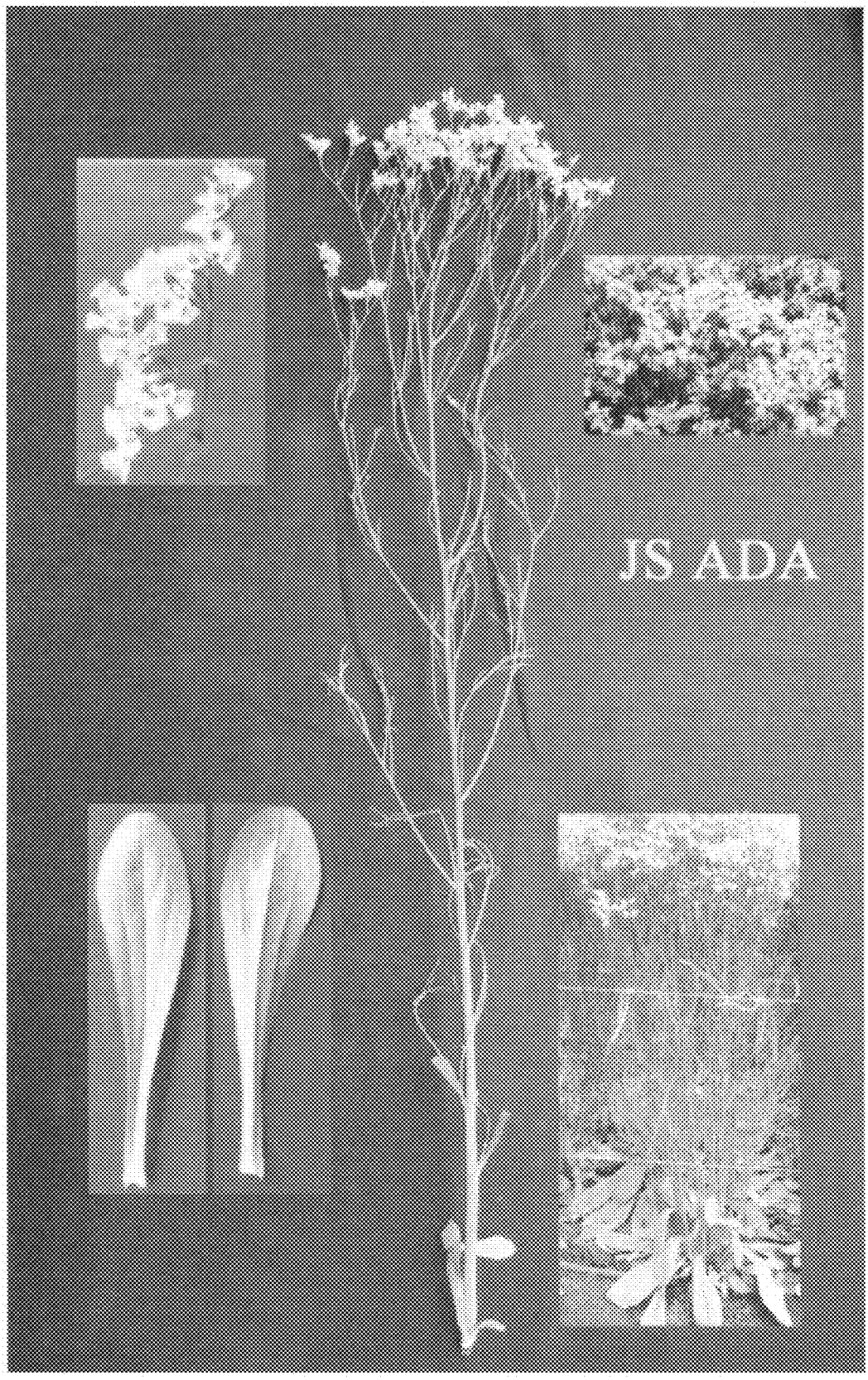
JS ADA